United States Patent [19]

Nakamoto et al.

[11] 4,144,741
[45] Mar. 20, 1979

[54] VOID DETECTING DEVICE

[75] Inventors: Koichiro Nakamoto; Nobumi Ohyama; Kiyoshi Adachi, all of Tokyo; Hajime Kuwahara, Musashino, all of Japan

[73] Assignees: Doryokuro Kakunenryo Kaihatsu-Jigyodan; Yokogawa Electric Works, Ltd., both of Tokyo, Japan

[21] Appl. No.: 782,238

[22] Filed: Mar. 28, 1977

[51] Int. Cl.$^2$ .................................... G01N 27/00
[52] U.S. Cl. ................................. 73/19; 73/194 EM; 324/204
[58] Field of Search .................. 73/19, 23, 53, 61 R, 73/194 EM; 324/34 FL, 34 TE, 36, 40, 204, 222, 225, 226, 227

[56] References Cited
U.S. PATENT DOCUMENTS

| | | | |
|---|---|---|---|
| 2,583,724 | 1/1952 | Broding | 73/194 EM |
| 3,529,234 | 9/1970 | Keen | 73/19 |
| 3,824,456 | 7/1974 | Wiegand | 324/34 FL |
| 4,014,206 | 3/1977 | Taylor | 73/19 |

Primary Examiner—Stephen A. Kreitman
Attorney, Agent, or Firm—Parmelee, Johnson, Bollinger & Bramblett

[57] ABSTRACT

A detector to be inserted into a flowing conductive fluid, e.g. sodium coolant in a nuclear reactor, comprising at least one exciting coil to receive an a-c signal applied thereto and two detecting coils located in the proximity of the exciting coil. The difference and/or the sum of the output signals of the detecting coils is computed to produce a flow velocity signal and/or a temperature-responsive signal for the fluid. Such flow velocity signal or temperature signal is rectified synchronously by a signal the phase of which is shifted substantially ± 90° with respect to the flow velocity signal or temperature signal, thereby enabling the device to detect voids in the flowing fluid without adverse effects from flow velocity variations or flow disturbances occurring in the fluid.

4 Claims, 9 Drawing Figures

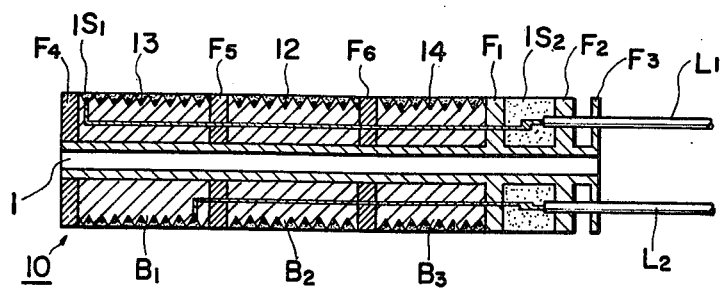
FIG. 6
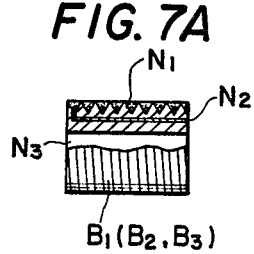
FIG. 7A  FIG. 7B
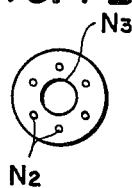
FIG. 8
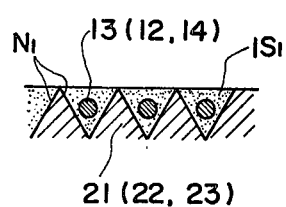
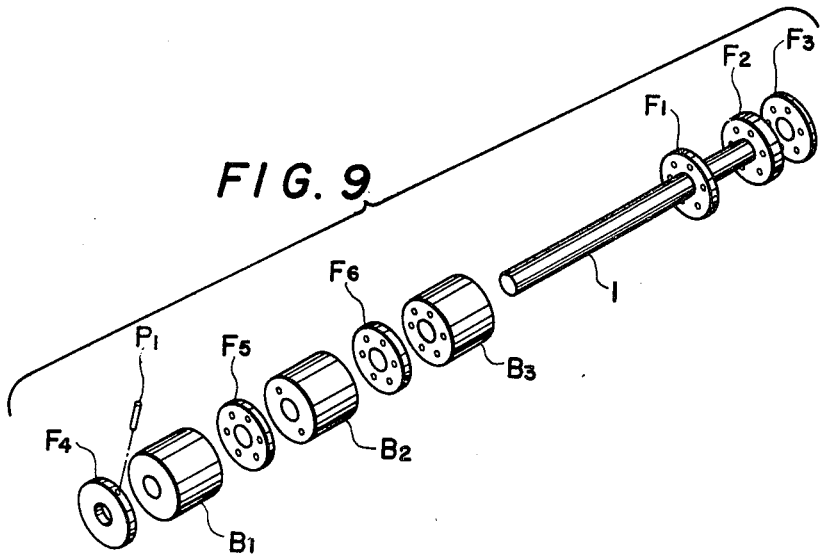
FIG. 9

VOID DETECTING DEVICE

BACKGROUND OF THE INVENTION

Field of the Invention

The present invention relates to a void detecting device. More particularly, this invention relates to a device especially adaped for detection of a void existing in a sodium coolant used in a nuclear reactor.

FIG. 1 illustrates the structure of an exemplary detector employed in the present invention, in which an exciting coil 12 is wound around a coil bobbin 11 and detecting coils 13 and 14 are wound around the coil bobbin 11 at positions on opposite sides of the exciting coil 12. The detector is inserted into a fluid to be measured and positioned so that the axial direction of the coil bobbin 11 is parallel to the fluid flowing direction F.

When an a-c signal is applied to the exciting coil 12, an eddy current is generated in the fluid. This eddy current can be divided broadly into two components, namely the one generated by the interaction of the conductive fluid and the magnetic flux from the exciting coil 12, and the one resulting from the vector product of the fluid velocity V and the main magnetic flux $\Phi$. The new magnetic flux caused by the latter interacts with the main magnetic flux from the exciting coil 12, and the one resulting from the vector product of the fluid velocity V and the main magnetic flux $\Phi$. The new magnetic flux caused by the latter interacts with the main magnetic flux from the exciting coil 12, so that the flux distribution in the vicinity of the exciting coil 12 is distorted from the normal state shown by the solid line (a) in FIG. 2 to the state represented by the dotted line (b).

It is known that the amount of the flux distribution change corresponds to the fluid flow velocity. It also is known that the magnitude of the eddy current caused by the main magnetic flux $\Phi$ corresponds to the fluid temperature. Accordingly, it is possible to determine the fluid flow velocity by computing the difference between the output signals $e_1$ and $e_2$ of the detecting coils 13 and 14. It also is possible to determine the fluid temperature by computing the sum of the output signals $e_1$ and $e_2$.

The term "void" is used herein to denote the presence in the flowing fluid of a substance other than the conductive fluid, such as a bubble or a gas mixed into the fluid. If the conductive fluid contains a void, such void disturbs the symmetry of the eddy current distribution in the vicinity of the exciting coil 12. This disturbance increases the apparent level of the flow velocity output signal $(e_1 - e_2)$ or of the fluid temperature output signal $(e_1 + e_2)$, or produces a fluctuation in the output signal.

Theoretically, it is possible to detect the presence or absence of a void through detection of the level increase or amplitude fluctuation in the output signals $(e_1 - 3_2)$ or $(e_1 + e_2)$. However, the flow velocity or temperature of the fluid to be measured is not of a fixed value and continuously varies slightly, thereby varying the value of output signals $(e_1 - e_2)$ and $(e_1 + e_2)$. In practice, it becomes difficult to discern whether such variation results from the level increase or amplitude fluctuation in the output signal caused by the presence of a void, or from the change in the flow velocity or temperature. Thus accurate detection of a void is not attainable by use of devices known to the art.

SUMMARY OF THE INVENTION

The object of the present invention is to provide a detector of the type having simple structure that can be inserted into a conductive fluid for the purpose of detecting with high sensitivity a void existing in the fluid.

Towards achieving that object, we have observed the phase of a flow velocity signal $(e_1 - e_2)$, a temperature signal $(e_1 + e_2)$, and a void signal, and have found the following, though there are some variations depending upon the kind of fluid used and the frequency of the exciting signal:

(i) The maximum sensitivity is attained in the flow velocity signal when its phase is substantially coincident with that of the exciting signal.

(ii) In the temperature signal obtained in the case of using a nonmagnetic material for a coil bobbin, the maximum sensitivity is attained when its phase has a difference of $+60°$ to $+70°$ from the exciting signal.

(iii) Although the void signal has no fixed phase, as it is based on the probability from the cause of generation, the maximum sensitivity is attained when its phase has a difference of $+70°$ to $+90°$ from the flow velocity signal or exciting signal.

FIG. 3 is a vector diagram showing the phase relations among the flow velocity signal, temperature signal and void signal, in which the oblique line plots the region where the void signal exists.

In view of the above-described observations, and according to the present invention, a void signal is detected independent of a flow velocity signal or a temperature signal by synchronized rectification of the flow velocity or temperature signal by a signal of which the phase is shifted approximately $\pm 90°$ relative to the flow velocity or temperature signal.

BRIEF DESCRIPTION OF THE DRAWINGS

FIG. 6 is a sectional view of the concrete structure of an exemplary detector employed in the invention;

FIG. 7 illustrates the structure of a coil bobbin used in FIG. 6, in which (A) is a partially sectional side view and (B) is a front view;

FIG. 8 is an enlarged view of the screw threads in FIG. 7; and

FIG. 9 is an assembly diagram of the detector of FIG. 6.

DESCRIPTION OF THE PREFERRED EMBODIMENT

Figure 1:
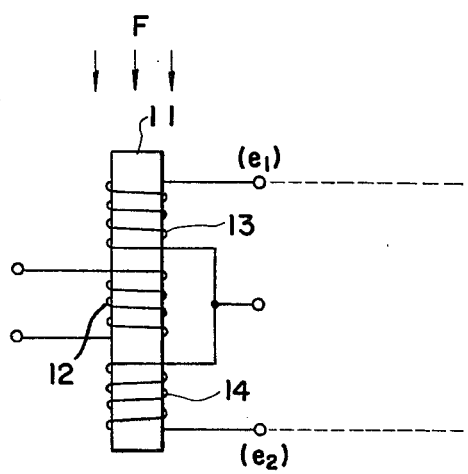
FIG. 1 illustrates the structure of an exemplary detector employed in the present invention.
Figure 2:
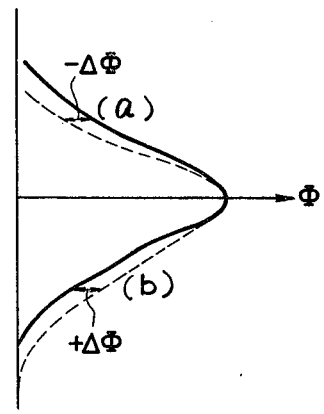
FIG. 2 is an explanatory diagram plotting the operation of the detector shown in FIG. 1.
Figure 3:
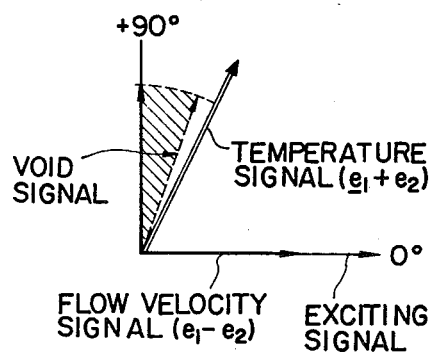
FIG. 3 is a vector diagram representing the phase relations among a flow velocity signal, a temperature signal and a void signal obtained from the detector of FIG. 1.
Figure 4:
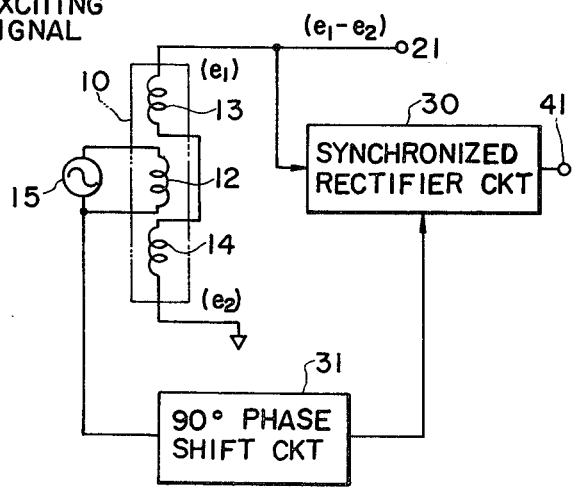
FIG. 4 is a block diagram of a detecting device embodying the present invention.

Referring now to FIG. 4, which is a block diagram showing an embodiment of the present invention, the detector of FIG. 1 is shown at 10. This detector comprises an exciting coil 12 with detecting coils 13 and 14 disposed on opposite sides thereof, an oscillator 15 whose output terminals are connected to the exciting coil 12, an output terminal 21 through which a flow velocity signal ($e_1 - e_2$) is obtained, a synchronized rectifier circuit 30, and a 90° phase shifter 31.

The rectifier circuit 30 receives the flow velocity signal ($e_1 - e_2$) and rectifies it synchronously by a signal produced from the phase shifter 31 and having a phase shifted + 90° from the flow velocity signal. Consequently, the signal component related to the flow velocity becomes ($e_1 - e_2$) cos 90° = 0, and thus, only the + 90° component or void signal included in the flow velocity signal ($e_1 - e_2$) is present at the output terminal 41.

Figure 5:
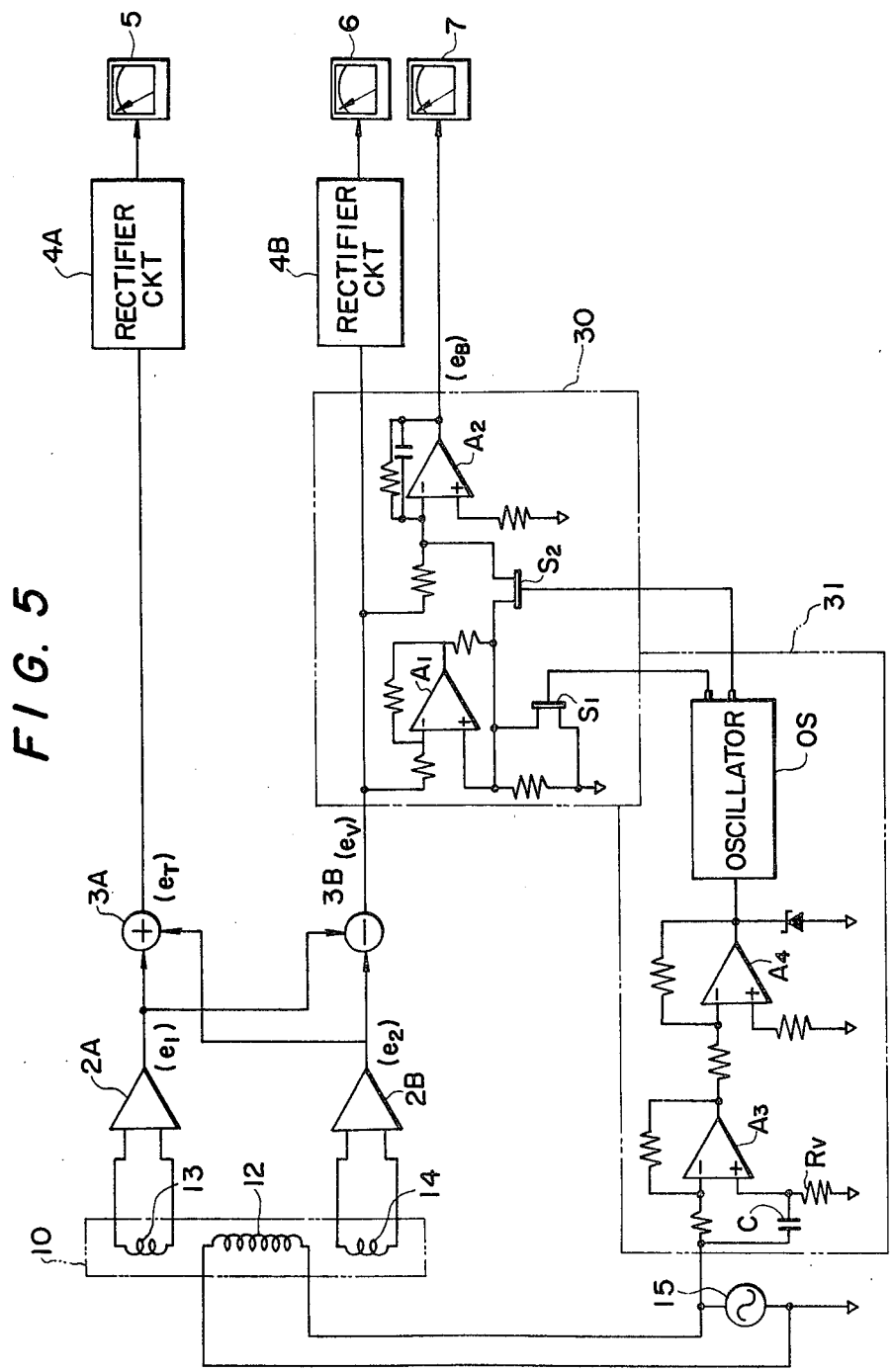
FIG. 5 is a circuit diagram implementing the device of FIG. 4.

FIG. 5 is a circuit diagram showing an embodiment implementing the device of FIG. 4, wherein the parts corresponding to those in FIG. 4 are labeled with the same symbols. The embodiment illustrated in FIG. 5 comprises an amplifier 2A for amplifying the output signal of the detecting coil 13, an amplifier 2B for amplifying the output signal of the detecting coil 14, an adding circuit 3A for adding the output signal $e_1$ of the amplifier 2A and the output signal $e_2$ of the amplifier 2B to produce a temperature signal $e_T$, a subtracting circuit 3B for subtracting the output signal $e_2$ of the amplifier 2B from the output signal $e_1$ of the amplifier 2A to produce a flow velocity signal $e_V$, rectifier circuits 4A and 4B, and indicators 5 and 6 so connected that the former indicates the temperature of the fluid to be measured while the latter indicates the flow velocity of the fluid.

The synchronized rectifier circuit 30 comprises an operational amplifier $A_1$ receiving the flow velocity signal $e_V$ from the subtracting circuit 3B, an operational amplifier $A_2$ across which a feedback circuit is formed by parallel connection of a resistor and a capacitor, and series-parallel switch circuits $S_1$ and $S_2$ connected between the output and input terminals of the operational amplifiers $A_1$ and $A_2$. An indicator 7 serves to indicate the void signal $e_B$ obtained from the synchronized rectifier circuit 30.

The 90° phase shifter 31 consists of an operational amplifier $A_3$ receiving the output signal of the oscillator 15 through a phase-shift circuit formed of a resistor $R_V$ and a capacitor C, an amplifier $A_4$ for amplifying the output of operational amplifier $A_3$, and a rectangular-wave oscillator OS which receives the output of amplifier $A_4$ as a trigger signal and generates a pulse signal to drive the switches $S_1$ and $S_2$ to the synchronized rectifier circuit 30.

The phase of the output pulse signal obtained from rectangular-wave oscillator OS is variable to + 90° or any other angle with respect to the exciting signal (output of oscillator 15) by adjusting the value of the resistor $R_V$. In the synchronized rectifier circuit 30, switches $S_1$ and $S_2$ are actuated by the output pulses of the rectangular-wave oscillator OS in such a manner that when one is turned on, the other is turned off and vice versa. In the state where switch $S_1$ is off and switch $S_2$ is on, the signal component of flow velocity signal $e_V$ is fed to the amplifier $A_2$ through the amplifier $A_1$, so that a + 90° component or void signal $e_B$ included in the flow velocity signal $e_V$ is obtained from the output terminal of the amplifier $A_2$ without being influenced or affected by the flow velocity signal $e_V$.

In this embodiment, although the phase of the signal for actuating switches $S_1$ and $S_2$ is shifted + 90°, the shift may also be − 90°. Moreover, instead of applying the flow velocity signal $e_V$ to the input terminal of the synchronized rectifier circuit 30, the temperature signal $e_T$ may be applied thereto. In this situation, the signal for actuating the switches $S_1$ and $S_2$ is to be adjusted so that its phase is shifted ± 90° against the temperature signal $e_T$. Through synchronized rectification of the temperature signal $e_T$ by the ± 90° phase-shifted signal, the void signal component included in the temperature signal can be detected without being influenced by the temperature signal.

FIG. 6 illustrates the structure of an exemplary detector employed in the present invention. In this drawing, a hollow shaft 1 of the detector has flanges $F_1$, $F_2$, $F_3$ on its one (right) end. The shaft may be composed of either magnetic material such as iron or nonmagnetic material such as stainless steel. Coil bobbins $B_1$, $B_2$ and $B_3$ are composed of electrically-insulating material such as ceramic, and the outer surfaces of the bobbins are formed into screw threads $N_1$ each having a V-shaped cross section as illustrated in FIG. 7. Each bobbin has a plurality of through-holes $N_2$ for permitting pass-through of leads and also an axial hole $N_3$ for insertion of the shaft 1. The center coil 12 on bobbin $B_2$ functions as an exciting coil, while the outer coils 13 and 14 on bobbins $B_1$ and $B_3$ function as detecting coils.

As shown in FIG. 8, the three coils are composed of uncovered or uncoated core wires wound along the screw threads $N_1$. Insulator material $IS_1$ filling the screw threads $N_1$ serves to hold the coils in relatively fixed positions and also to maintain electrical insulation. Flanges $F_4$, $F_5$ and $F_6$ have a plurality of through-holes for permitting pass-through of leads and also an axial hole for insertion of the shaft 1. These flanges hold the coil bobbins $B_1$, $B_2$ and $B_3$ so as to set the coils at predetermined positions, and may be composed of either magnetic or nonmagnetic material. The flanges are not always necessary if formed integrally with the coil bobbins. Leadwires $L_1$, $L_2$ are composed of, for example, mineral insulated wires and are connected to the ends of the coil leads between flanges $F_1$ and $F_2$. Insulator material $IS_2$ serves to fix the joints between leadwires $L_1$, $L_2$ and the ends of coil leads as well as to maintain insulation.

A detector of such structure is manufactured in the following manner. Coil bobbins previously equipped with wound coils are inserted sequentially to shaft 1 with flanges being interposed as illustrated in FIG. 9; simultaneously, both ends of each coil are drawn out to form leads between flanges $F_1$ and $F_2$ via the through-holes in the flanges and also via the axial hole formed in each coil bobbin. In applications where the flanges are composed of stainless steel, bushes are fitted into the through-holes so as to prevent contact of the coil leads with the flanges. Subsequently, the flange $F_4$ is secured to the shaft 1 by a pin $P_1$ or the like, and between flanges $F_1$ and $F_2$, coil-to-coil connection and coil-to-leadwire connection are made by the use of spot-welding or the like.

Axial slippage of each coil bobbin on the shaft 1 is prevented by means of a pin 9, and circumferential slippage is prevented by providing grooves and protrusions engageable axially with each other on the shaft 1 and the through-holes. Leadwires $L_1$ and $L_2$ are anchored to the shaft 1 by welding the leadwire coverings and thin portions of flanges $F_3$ by the use of a small torch such as plasma welder. Finally, the screw threads $N_1$ of the coil bobbins and the space between flanges $F_1$ and $F_2$ are filled with insulating material to finish the process.

In the detector thus obtained, complete insulation is attained between the coils by the screw threads, thereby allowing the use of a bare wire for each coil. Moreover, there is a further advantage that permits previous provision of individual coils around a plurality of coil bobbins and is completed by inserting the coil bobbins sequentially to the shaft, thereby facilitating manufacture.

According to an important aspect of the invention, as described hereinabove, the synchronized rectification of a flow velocity signal or a temperature signal is effected by a ± 90° phase-shifted signal to accomplish detection of a void signal discriminatively from the flow velocity signal or temperature signal. The device is capable of detecting with high sensitivity a void existing in the fluid to be measured.

We claim:

1. A void detecting device comprising a detector having at least one exciting coil to receive an a-c signal applied thereto and two detecting coils provided in the proximity of said exciting coil, said detector being adapted to be inserted into a conductive fluid to be measured; and a circuit for obtaining a flow-or-temperature-responsive output signal by combining signals of said two detecting coils; the improvement wherein a void signal is obtained comprising:

synchronized rectification means having first and second inputs and a void signal output;

means coupling said flow-or-temperature-responsive output signal to said first input; and means coupling to said second input a signal the phase of which is shifted substantially ± 90° with respect to said flow-or-temperature-responsive output signal.

2. The void detecting device as claimed in claim 1, wherein said synchronized rectification means comprises an operational amplifier ($A_1$) receiving the output signal, an operational amplifier ($A_2$) with a feedback circuit formed of a parallel connection of a resistor and a capacitor, and series-parallel switches ($S_1$ and $S_2$) connected between the output and input terminals of said operational amplifiers ($A_1$ and $A_2$) and means for turning said switches ($S_1$ and $S_2$) on or off by said signal of which the phase is shifted substantially ± 90°.

3. The void detecting device as claimed in claim 1, wherein said detector comprises a shaft, a plurality of coil bobbins to receive said shaft therein and comprised of insulation material with screw threads formed on the outer surface thereof; coils wound along said screw threads; the ends of said coils being drawn out to one end of said shaft by way of the insides of said coil bobbins.

4. The void detecting device as claimed in claim 3, wherein said coil bobbins are inserted sequentially to the shaft, flanges being interposed among the bobbins; and the ends of said coils being drawn out to one end of the shaft serving as leads passing through holes formed in said flanges and coil bobbins.

* * * * *